Figure 1:
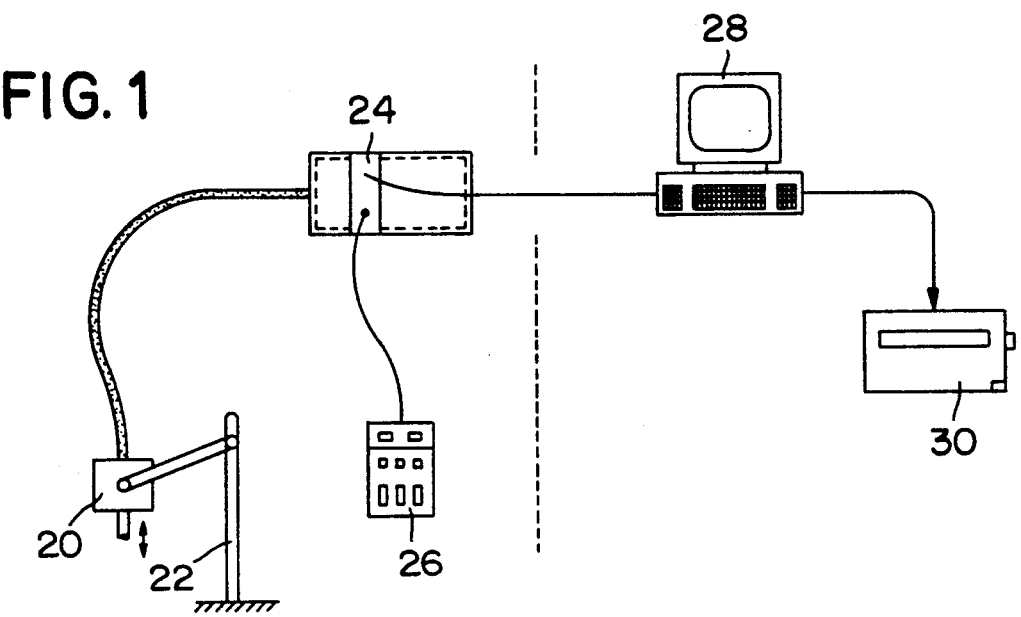

United States Patent [19]

Schumacher et al.

[11] Patent Number: 5,195,532
[45] Date of Patent: Mar. 23, 1993

[54] APPARATUS FOR PRODUCING A STIMULATION BY VIBRATION OF A TAPPET WHICH IS PUT ON A HUMAN'S SKIN

[75] Inventors: Walter Schumacher, Ohrum; Walter Wetzel, Brunswick; Gerd Hollnagel, Brunswick; Gerald Arndt, Brunswick; Ulrich Plüquett, Göttingen; Arno May, Göttingen; Dietmar Oberdorfer, Göttingen; Heiko Baden, Schneverdingen, all of Fed. Rep. of Germany

[73] Assignee: Phywe Systeme GmbH, Fed. Rep. of Germany

[21] Appl. No.: 706,395

[22] Filed: May 28, 1991

[30] Foreign Application Priority Data

May 29, 1990 [DE] Fed. Rep. of Germany ....... 4017251

[51] Int. Cl.$^5$ .................... A61B 5/00; A61B 19/00; A61H 7/00; A61H 23/00
[52] U.S. Cl. .................... 128/739; 128/740; 128/52; 128/55
[58] Field of Search ............ 128/52, 54, 55, 32, 128/44, 739, 740

[56] References Cited

U.S. PATENT DOCUMENTS

| | | | |
|---|---|---|---|
| 3,739,768 | 6/1973 | Rieth | 128/740 |
| 4,235,243 | 11/1980 | Saha | 128/740 |
| 4,326,507 | 5/1982 | Barkalow | 128/54 |
| 4,485,823 | 12/1984 | Yamaguchi et al. | 128/739 |
| 4,566,442 | 1/1986 | Mabuchi et al. | 128/55 X |
| 4,646,754 | 3/1987 | Seale | 128/649 X |
| 4,771,792 | 9/1988 | Seale | 128/649 X |
| 4,788,968 | 12/1988 | Rudashevsky et al. | 128/55 X |
| 5,024,239 | 6/1991 | Rosenstein | 128/739 X |
| 5,083,552 | 1/1992 | Lipowitz | 128/44 |

*Primary Examiner*—Mickey Yu
*Assistant Examiner*—Brian E. Hanlon
*Attorney, Agent, or Firm*—Eckert Seamans Cherin & Mellott

[57] ABSTRACT

The apparatus for producing mechanical stimulations by vibration of a tappet which is put on a human's skin comprises a measuring head, which on one hand has a housing, in which the back and forward moving tappet is arranged and on the other hand an actuating unit for this tappet. An acceleration sensor is attached to the tappet.

11 Claims, 1 Drawing Sheet ent it is intended to precisely determine the force of
APPARATUS FOR PRODUCING A STIMULATION BY VIBRATION OF A TAPPET WHICH IS PUT ON A HUMAN'S SKIN The invention relates to an apparatus for producing a mechanical stimulation by vibrating a tappet (plunger, mechanical stimulator) which is put on a human's skin. The device has a measuring head which comprises on one hand a housing in which the back and forward moving tappet is arranged and on the other hand an actuating unit for the tappet.

The perception of mechanical vibrations can be tested with a device of this kind, so that e.g. under a timely inclining or declining amplitude of mechanical vibration a threshold value for the perception of the vibration can be given by a person tested (patient). From this assertions can be made about the conductance of the larger-caliber medullated afferent nerve fibers (of the tactile sense). By comparing with normal data of healthy patients or with the data of the same patient obtained in earlier measurements and under comparable conditions an early diagnosis can be made for sensible polyneuropathy, e.g. in conjunction with diabetes mellitus, nephritic disorders, multiple sclerosis and spinal cord diseases.

In the known device of the kind mentioned above the amplitude of the vibration of the tappet can be adjusted. The amplitude is measured by means of a photoelectric barrier as the elongation with reference to the main mass of the measuring head.

In the known device the amplitude strongly depends on the force acting on the tappet and pressing it onto the skin, as well as on an external attenuation means of the tappet. Especially for small amplitudes it is difficult, to obtain a reliable reading and hence an evaluation of the amplitude. The value of the amplitude is not sufficiently reproducible. Finally the force of application is indicated only in a few, coarse steps, this complicates the reproducibility of a measurement with the known device.

Starting from the apparatus of the kind mentioned above the invention has the aim to further develop this apparatus so that independent of the application force onto the skin of a human and independent of a possible external attenuation the amplitude of the vibration of the tappet can be exactly and thus reproducibility predetermined and kept. Thereby the amplitude does not depend from the force of application. In a further development it is intended to precisely determine the force of application, so that hereby the measurements are better reproducible.

This aim is achieved by an apparatus which incorporates starting with the features of the above mentioned kind a sensor for acceleration arranged at the tappet.

In accordance with the invention the acceleration of the tappet is continuously measured during its periodic back and forward movements. The acceleration signal thus obtained is used for controlling the actuation unit of the tappet. By this the amplitude of the vibration can be exactly predetermined and kept during the measurement independent of the force of application or a possible attenuation. Furtheron by integration a velocity information can be obtained from the acceleration signal and an information about the local position is available by a further integration.

In a preferred embodiment the tappet of the actuating device and/or the acceleration sensor are electrodynamic, this means they exhibit a permanent magnet and a coil, respectively, the coil being in the magnetic field of the permanent magnet. An actuating unit of this kind acts in both directions of drive, thereby contrary to an actuating unit operating only in one direction, which actuating unit needs a spring for the back stroke, a better equilibrated movement of vibration is obtained. Furtheron the preferred acceleration sensor of this kind delivers a signal in both directions of movement of the tappet, whereby the two signals have a different polarity. This allows for an examination whether the forward stroke is indeed identical with the backwards stroke, or not; deviations in the two directions of movement may be compensated by a control unit.

In another embodiment the acceleration sensor is piezoelectric. This construction has the advantage of a rather rugged, simple lay-out. The sensor is attached to the tappet only and has no parts to be fixed at the housing, thereby a precise guidance between tappet and housing is unnecessary, because there is no need to precisely maintain an air gap etc. as in the electrodynamic embodiment.

In a further, preferred embodiment the acceleration sensor is connected to an integrator, the output thereof is connected to the actuating unit. Thereby a control is achieved for constant amplitude of the movements of vibration of the tappet, if feed back prevails. If the amplitude of the movement of a tappet becomes larger the signal delivered from the acceleration sensor becomes larger, too, this signal after integration is used to diminish the actuation of the tappet.

In another preferred embodiment a double integrator follows the acceleration sensor to obtain an information about the local position of the tappet in time.

In a preferred embodiment springs are arranged between the tappet and the housing, whereby these springs on one hand determine the application force of the tappet and on the other hand in a preferred embodiment are axially fixed to the tappet in the housing. For this at least two spring blades are provided arranged in an axially offset manner in the preferred embodiment.

In a further preferred embodiment a sensor for measuring the displacement between the tappet and the housing is attached to the at least one spring fixing the tappet in the housing. The force can be measured with this sensor and knowing the elastic constant of the at least one spring for pulling the tappet into the housing or pushing it out of the housing.

Furtheron it is advantageous to allow for adjustment of the frequency of the movement of the tappet, i.e. especially to connect the actuating unit to a generator having a variable frequency thereby tactile stimulations are obtained at different vibration frequencies and in addition the relation of the perception of a patient from the frequency of the movements of the tappet can be studied.

Finally in a further embodiment the measuring head (vibrator) is releaseably fixed to an adjustable articulated arm. The vibrator can thus be applied to different areas of the patient. If released from the articulated arm the vibrator can be applied manually.

Further advantages and features of the invention result from the remaining claims as well as from the following detailed description of a non limiting embodiment, which is going to be explained under reference to the drawing. The drawing shows in:

FIG. 1 a principal sketch in block diagram of the complete device and

Figure 2:
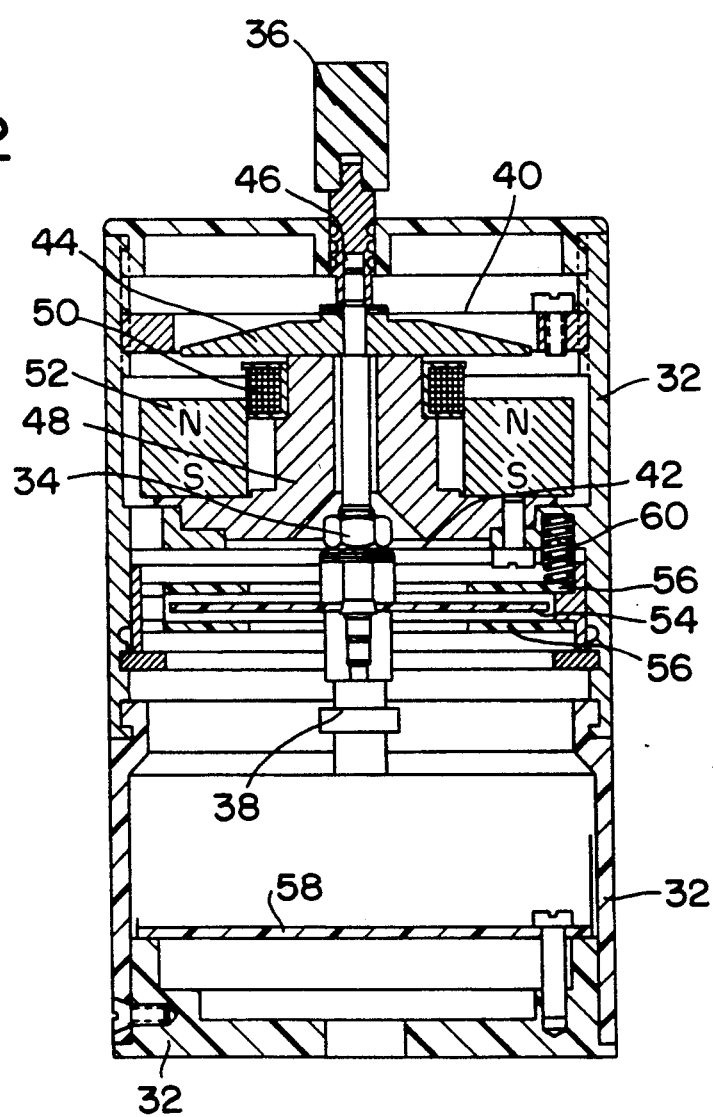

FIG. 2 an axial section through a measuring head.

The apparatus according to FIG. 1, named quantitative tester of the perception of vibration or vibration tester, too, consists of the following building blocks: measuring head 20, holder 22 for the measuring head 20, control electronics 24, patient reaction or control panel 26 and personal computer 28 with a printer 30 connected. The holder 22 is attached to a stand or a similar support and is provided for holding the measuring head 20 in different angular positions and different local areas so that the measuring head can be attached to any skin area of a patient and is held in this position.

In the control electronics 24 processing of the signals of the sensors of the measuring head takes place, furtheron the control electronics comprise the electric circuitry for the actuating unit of the measuring head.

The control panel 26 has five illuminated areas and three touch controls, the latter are marked in different colors. Furtheron a buzzer is provided for producing two signaling sounds. The control panel 26 for the patient receives information from the patient about him or her perceiving a tactile stimulation or not. The relevant touch control to be pressed for a specific program of examination is indicated by a light signal.

The measuring head 20 has a generally cylindrical housing in which is arranged a tappet 34 axially movable back and forth, it protrudes from one of the cylindrical faces of the housing 32 and ends there is a tappet head 36. A piezoelectric acceleration sensor (type PCB 303 A11) is arranged at the other end within the housing 32.

The tappet 34 is on one hand axially guided within the housing 32 and on the other hand elastically attached to the housing 32 by an upper blade spring 40 and a lower blade spring 42.

The tappet head 36 has a plastic part having a diameter of ten millimeters. This part can be exchanged, i.e. it can be replaced if damaged or for cleaning (sterilization) by screwing it from the tappet 34.

An electrodynamic actuating unit for the tappet 34 is arranged between the two blade springs 40, 42, which are arranged in a distance as large as possible. For this tappet 34 is attached to a disk-like pole plate 44 made of ferromagnetic material and clamped between an upper part 46 made of plastic of the tappet 34 and attached to the tappet 36 and a shoulder of a bolt-like main portion of the tappet 34. A pole core 48 is arranged immediately below the pole plate 44 and separated therefrom by an air gap of about 0.1 mm, the pole core 48 being as well manufactured of a ferromagnetic material. It is surrounded by a coil 50 which is arranged in direct vicinity of the pole plate 44. A ring shaped magnet is arranged outside and below this coil 50, the polarity thereof is indicated.

When the coil 50 is excited by an alternating current a back and forth movement of the pole plate 44 and thereby of the tappet 34 results. Depending upon the drive current through the coil 50 amplitudes between 0 and 0.15 mm may be adjusted. The vibration mode is sinusoidal. Coil 50 is connected to an adjustable frequency generator arranged in the control electronics 24, a power amplifier follows this generator and is likewise arranged in the control electronics 24, its output being connected to the coil 50.

Below the lower blade spring 42 and in direct vicinity thereof a condensor arrangement is provided. It serves to measure the displacement of the two blade springs 40, 42 and thus the tappet 34 out of the normal position (unbended springs 40, 42). If the tappet head 34 is placed onto the skin of a patient a certain application pressure is exerted leading to a bending of the two blade springs 40, 42. The value of this displacement is measured with a condensor arrangement. The displacement may amount (in both directions) to 1 mm. The actual application force is shown on the monitor of the computer 28 by a bar.

A disk-shaped intermediate sensor plate 54 is fixed to the tappet 34 and is arranged between two ring shaped sensor plates 56 attached to the housing 32. In the normal position shown the distance between the intermediate sensor plate 54 and the two sensor plates 56 has the same value. If the intermediate sensor plate 54 is displaced by moving tappet 34 out of its normal position the capacity of the arrangement changes. This alteration of the capacity is used to obtain an information about the displacement.

The two sensor plates 56 are adjusted in normal position of the tappet, so that they have uniform distance from the intermediate sensor plate 54. Adjustment is facilitated by an adjustment spring 60.

In the lower compartment of the housing 32 a circuit board 58 is arranged for the electronic components of the condensor arrangement.

What is claimed is:

1. An apparatus for testing a threshold of perception of mechanical vibration by producing a mechanical stimulation by vibration of a tappet applied to a patient's skin, wherein an amplitude of the mechanical vibration can be varied around a threshold of perception, the apparatus comprising:
    a measuring head, including a housing and a tappet elastically held in the housing and guided for back and forward movement;
    a tippet actuating unit attached to the tappet;
    an acceleration sensor attached to the tappet and connected to control electronics, the control electronics being attached to the measuring head and including a power amplifier attached to the tappet actuating unit; and,
    a patient reaction panel attached to the control electronics, the patient reaction panel including means for receiving a response from the patient to indicate a reaction upon perceiving a mechanical stimulation.

2. The apparatus according to claim 1, wherein the tappet is elastically held and guided in the housing by blade springs.

3. The apparatus according to claim 2, wherein a position sensor is arranged between said tappet and said housing.

4. The apparatus according to claim 3, wherein the position sensor arranged between said tappet and said housing comprises a condensor arrangement.

5. The apparatus according to claim 1, wherein the actuating unit of the tappet is electrodynamic and wherein a disk-shaped pole plate is fixed to the tappet and cooperates with a coil, a pole core and a permanent magnet which are fixed to the housing.

6. The apparatus according to claim 1, wherein the acceleration sensor is piezoelectric.

7. The apparatus according to claim 1, wherein an integrator follows the acceleration sensor, the output thereof being connected to the actuating unit of the tappet.

8. The apparatus according to claim 1, wherein the actuating unit comprises a generator whose frequency is adjustable.

9. The apparatus according to claim 1, further including means for displaying a value of the force of the tappet on the skin of a patient.

10. The apparatus according to claim 1, wherein the measuring head is releasably fixed to an adjustable swivel arm defined by a measuring head holder.

11. The apparatus according to claim 1, wherein the acceleration sensor is electrodynamic.

* * * * *